US007442199B2

(12) United States Patent
Teng

(10) Patent No.: US 7,442,199 B2
(45) Date of Patent: Oct. 28, 2008

(54) CLIP FOR ACUPUNCTURE NEEDLE

(76) Inventor: Hong Dar Teng, 28310 Industrial Blvd. #C, Hayward, CA (US) 94545

( * ) Notice: Subject to any disclaimer, the term of this patent is extended or adjusted under 35 U.S.C. 154(b) by 7 days.

(21) Appl. No.: 11/318,944

(22) Filed: Dec. 27, 2005

(65) Prior Publication Data

US 2007/0149992 A1 Jun. 28, 2007

(51) Int. Cl.
*A61B 17/34* (2006.01)

(52) U.S. Cl. ..................................................... 606/189

(58) Field of Classification Search ................. 606/205, 606/210, 130, 157, 158, 207, 211, 151, 219, 606/142, 222, 189; D28/39–40; 248/74.1–74.2; 206/380, 382, 574, 229; 403/109.6, 318, 403/319

See application file for complete search history.

(56) References Cited

U.S. PATENT DOCUMENTS 5,662,446 A * 9/1997 Haan .......................... 411/514
6,231,584 B1 * 5/2001 Gavronsky .................. 606/189
6,551,339 B2 * 4/2003 Gavronsky .................. 606/189
7,278,693 B2 * 10/2007 Smith et al .................. 301/113

* cited by examiner

*Primary Examiner*—Todd E. Manahan
*Assistant Examiner*—Christina D Gettman

(57) ABSTRACT

A one-hand operated acupuncture dispensing system to administer acupuncture treatment at an acupoint point is described. The system includes an acupuncture needle, a clip and a guide tube to house the needle and the clip for securing and releasing the needle inside the guide tube. The tube prevents the clip from separation from the tube after the needle is dispensed. The clip is shaped to allow the acupuncture needle to exit the guide tube at an angle. The clip and/or guide tube can provide color coding. An alternate to the system includes a cap that joins with a guide tube housing an acupuncture needle. This alternate system also includes a clip that secures and releases the needle. In this alternate system, the cap, as well as the clip and/or guide tube can provide color coding.

27 Claims, 6 Drawing Sheets

300

300

CLIP FOR ACUPUNCTURE NEEDLE

FIELD OF THE INVENTION

The present invention generally relates to acupuncture treatment. More specifically, the present invention pertains to a clip that secures an acupuncture needle longitudinally within a guide tube before acupuncture treatment and remains with the guide tube after the needle is released for acupuncture treatment.

BACKGROUND OF THE INVENTION

Acupuncture treatment of a human requires accessing acupoints in the human body with acupuncture needles. An acupuncture needle is an elongated shaft that has a sharp tip on one end. The sharp tip penetrates the human body through skin to access an acupoint or acupoints. Such an acupuncture needle is typically flexible, made of metal and its shaft generally is of a diameter similar to that of a fine sewing needle.

The sharp tip requires protection prior to accessing acupoints. Since the acupuncture needle has to penetrate through the skin to access an acupoint or acupoints under the skin in a human, the acupuncture needle has to remain sterile. Moreover, the slender and flexible structure of the needle requires support for the operator or acupuncturist to accurately point the needle at an acupoint and subsequently to push the needle through the skin of the human. Consequently a conventional design includes a slender guide tube encasing the needle. The guide tube not only protects the sharp tip till the needle is dispensed but also encloses the needle from the tip to part of a handle and thereby maintains its sterility.

In general, most prior conventional needle assemblies include a tab or stopper to secure the acupuncture needle in position inside the guide tube during storage, transport and handling. In such conventional acupuncture needle dispensing systems, the needle is required to stay longitudinal before, during and after the tab is removed, and while the needle is being dispensed. The tab jams the acupuncture needle toward one side of the interior of the guide tube core. Moreover in most conventional systems, while a first hand of an acupuncturist holds the guide tube with an acupuncture needle inside, a second hand is required to remove the tab to liberate the needle to move freely inside the core axially and laterally. The freed needle is then ready to be manipulated to access an acupoint.

A two-hand operation presents difficulty to the operator because the second hand may shift the position of the guide tube held by the first hand. Additionally to access some sideways or down facing acupoints, the guide tube has to be turned sideways or pointed down, which orientation may not be conveniently reached by two hands. Utilizing two hands on the acupuncture needle and guide tube also can distract the acupuncturist from the patient.

In addition, as an important shortcoming, in most conventional systems, the tab becomes separated from the guide tube. Due to its small size, the separated tab easily falls out and ends up on the floor, often in corners and crevices, making it very difficult to remove. Cumulatively, the separated tabs present unsightly debris or contamination in the professional office of a healthcare-provider.

Due to these shortcomings, conventional dispensing systems have been modified. Some modifications have taken the approach of replacing the conventional tab. Reference is made to U.S. Pat. No. 6,551,339 and U.S. Pat. No. 6,231,584. In both of these modifications, two hands of an operator are required to hold the tube and dispense the needle, and the needle loses the freedom to move laterally inside the guide tube for needle dispensing or insertion. A large force acts on the needle against the tube. Moreover, in the first modification, the elastic stopper that has been designed to replace a tab has to be removed from the tube to free the needle from the tube after insertion so that the tube can be removed. The elastic stopper is separated from the tube and becomes debris or contamination.

In the second modification, while a first hand holds the guide tube in place over an acupoint, a second hand is required to rotate a sleeve of a C-shaped configuration over a side slot to manipulate the handle of a needle for dispensing. It may well be due to these shortcomings, that the aforementioned modifications have not resulted in market adoption.

Thus, there is need for an improved system that allows a one-hand operation to dispense the needle, which system is equipped with a mechanism to hold the needle that allows it freedom to move axially and laterally during needle insertion but does not need to be removed after needle insertion.

SUMMARY OF THE INVENTION

The present invention satisfies this need. It presents a system and an associated method (collectively referred to herein as "the system" or "the present system") for an improved acupuncture needle dispensing system and supporting components. The invention is described in relation to a conventional acupuncture needle.

The present system includes an acupuncture needle, a guide tube to house the needle and a clip for securing and releasing the needle inside the guide tube. The needle is typical by having a small diameter section or a shaft and a larger diameter section or, in other words, a handle integral with the shaft.

The guide tube has a hollow core with open ends and a relatively rigid wall. The core is sized to allow the needle to freely move axially and laterally within the tube. In keeping with the invention, the tube is modified with windows to house the clip and the windows allow it to operate. In this connection, the clip has a narrow enclosure shaped by a first bend or, in other words, narrow bend with two members sized to hold or secure the acupuncture needle and a wide enclosure shaped by a second bend, or in other words, wide bend with two members, which wide bend is wider than the narrow bend. The wide enclosure is sized to allow the needle to pass through. A bridge connects the ends of the two members of the second bend or wide bend as will become apparent from the more detailed description in this arrangement. The needle is secured in the narrow enclosure and moves from the first or narrow enclosure to the second or wide enclosure for release.

Once released, the needle is free to move axially and laterally inside the guide tube. It may contact the guide tube during dispensing or insertion. However the frictional force from such contact is very small and does not substantially affect the free manipulation of the needle. In contrast, previous modifications either press the needle against the inner wall of the tube with a large frictional force or require a two-hand operation.

The present system includes two embodiments, a slide-through embodiment and a cap-on embodiment. The slide-through embodiment includes an acupuncture needle, a guide tube to house the needle and a clip for securing and releasing the needle inside the guide tube. The cap-on embodiment includes an acupuncture needle, a cap that connects with a guide tube to house the needle and a clip for securing and releasing the needle inside the cap and the guide tube. Both embodiments include the features of the invention.

BRIEF DESCRIPTION WITH REFERENCE TO THE ACCOMPANYING DRAWINGS

The various features of the present invention and the manner of attaining them will be described in greater detail with reference to the following description, claims, and drawings, wherein reference numerals appear in more than one drawing, where appropriate, to indicate a correspondence between the referenced items, and wherein:

Figure 1:
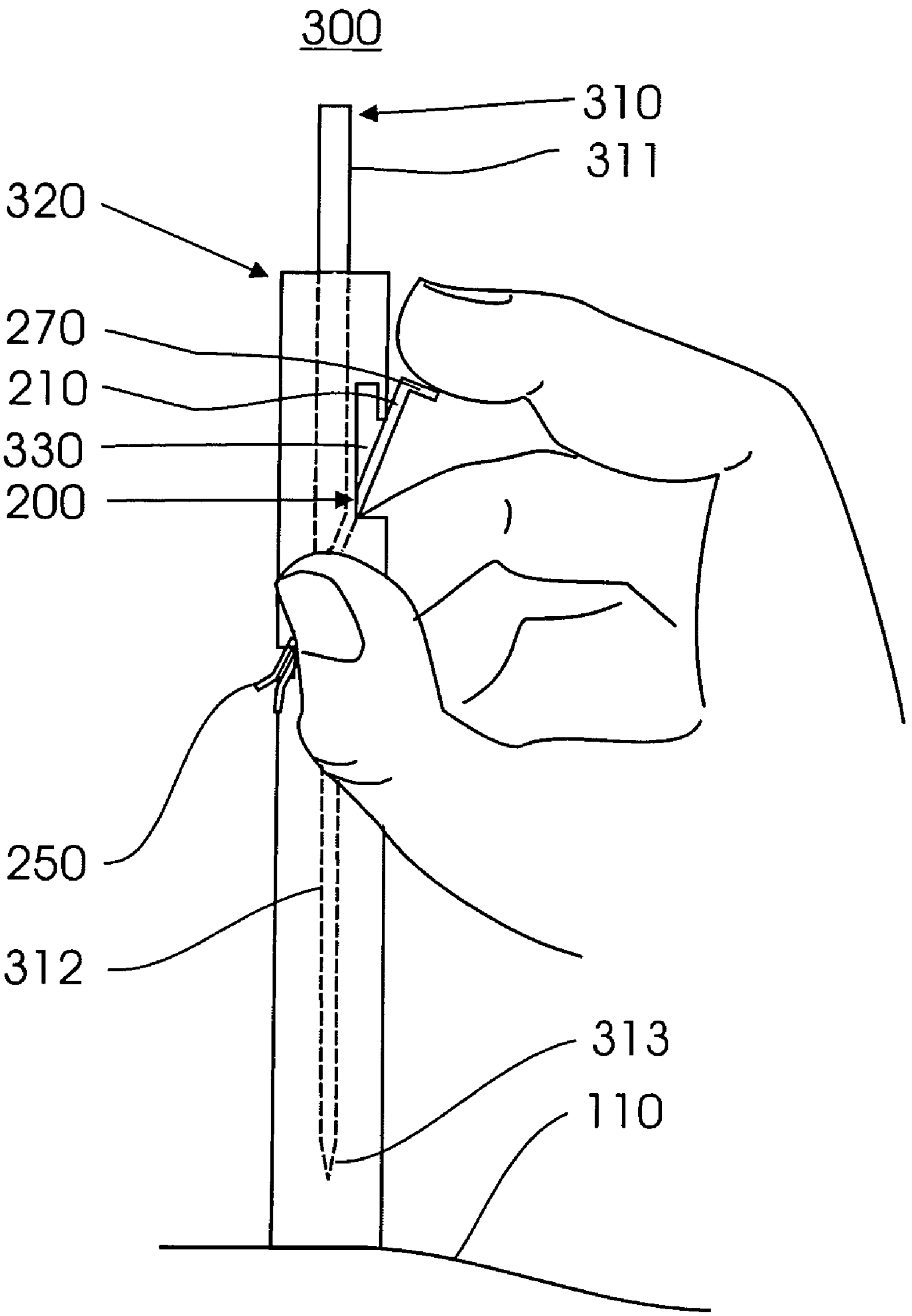
FIG. 1 is an acupuncture needle dispensing system of a slide through embodiment of the invention enabling a one-hand only operation.
Figure 4A:
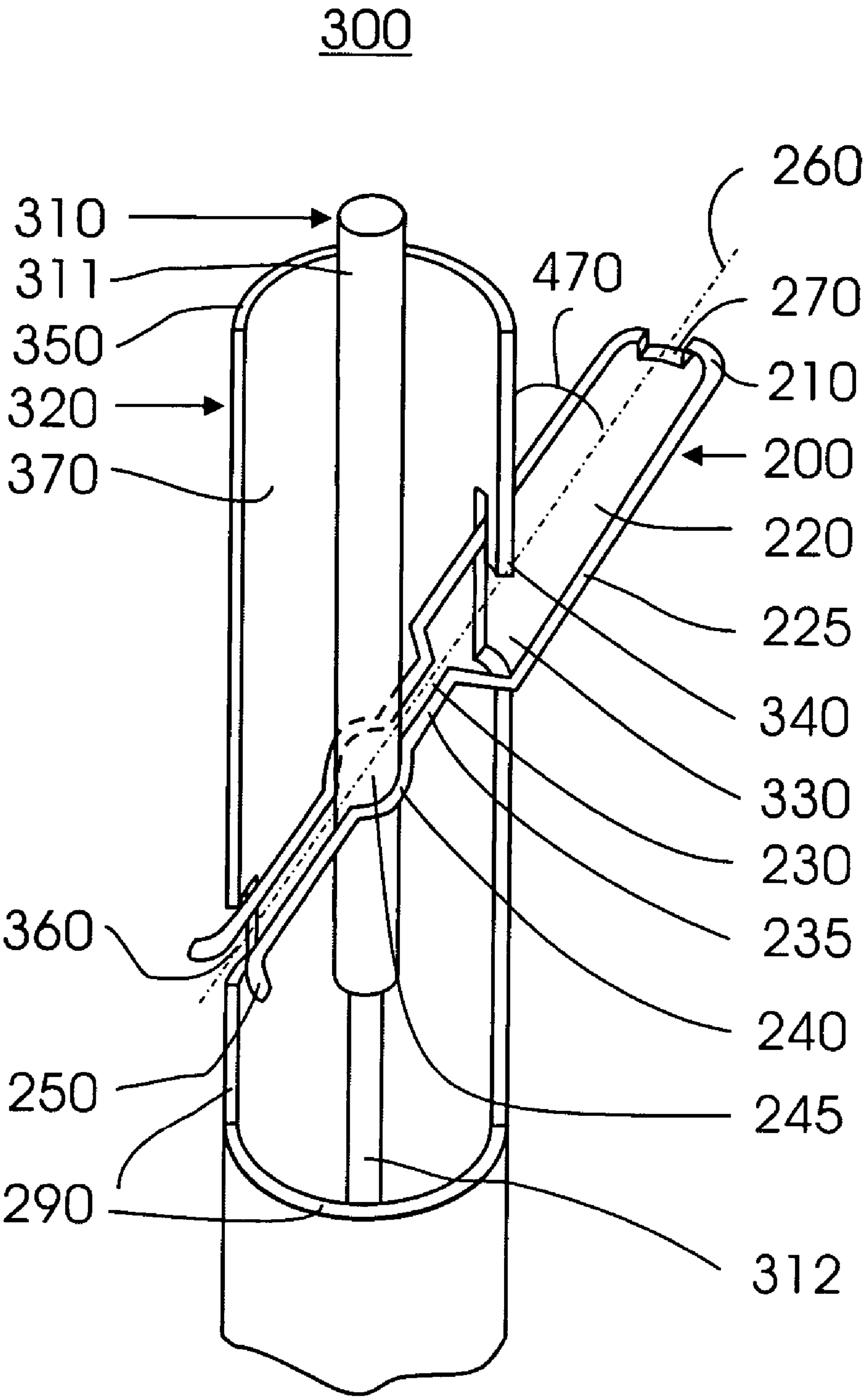
Figure 4B:
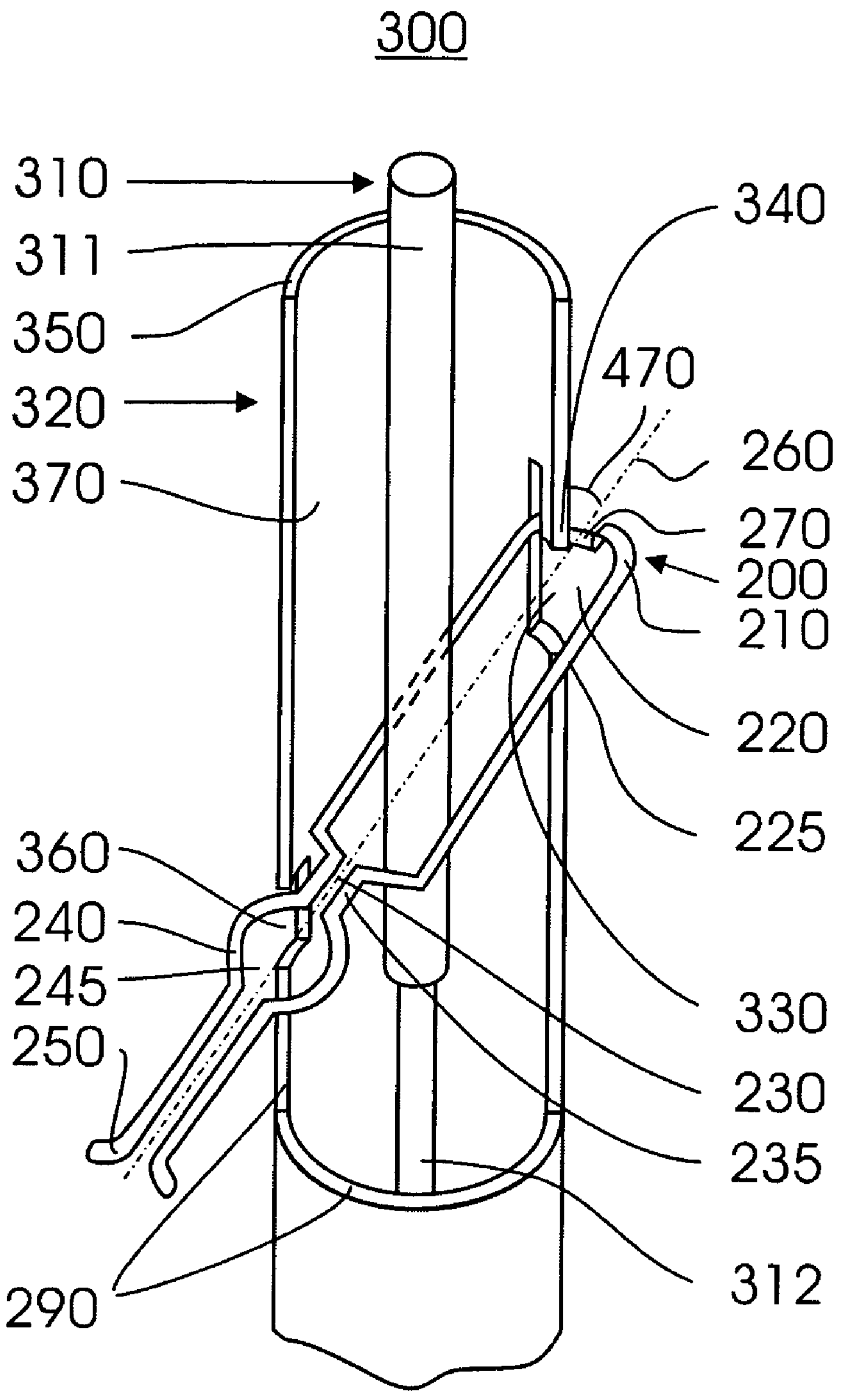
Figure 5:
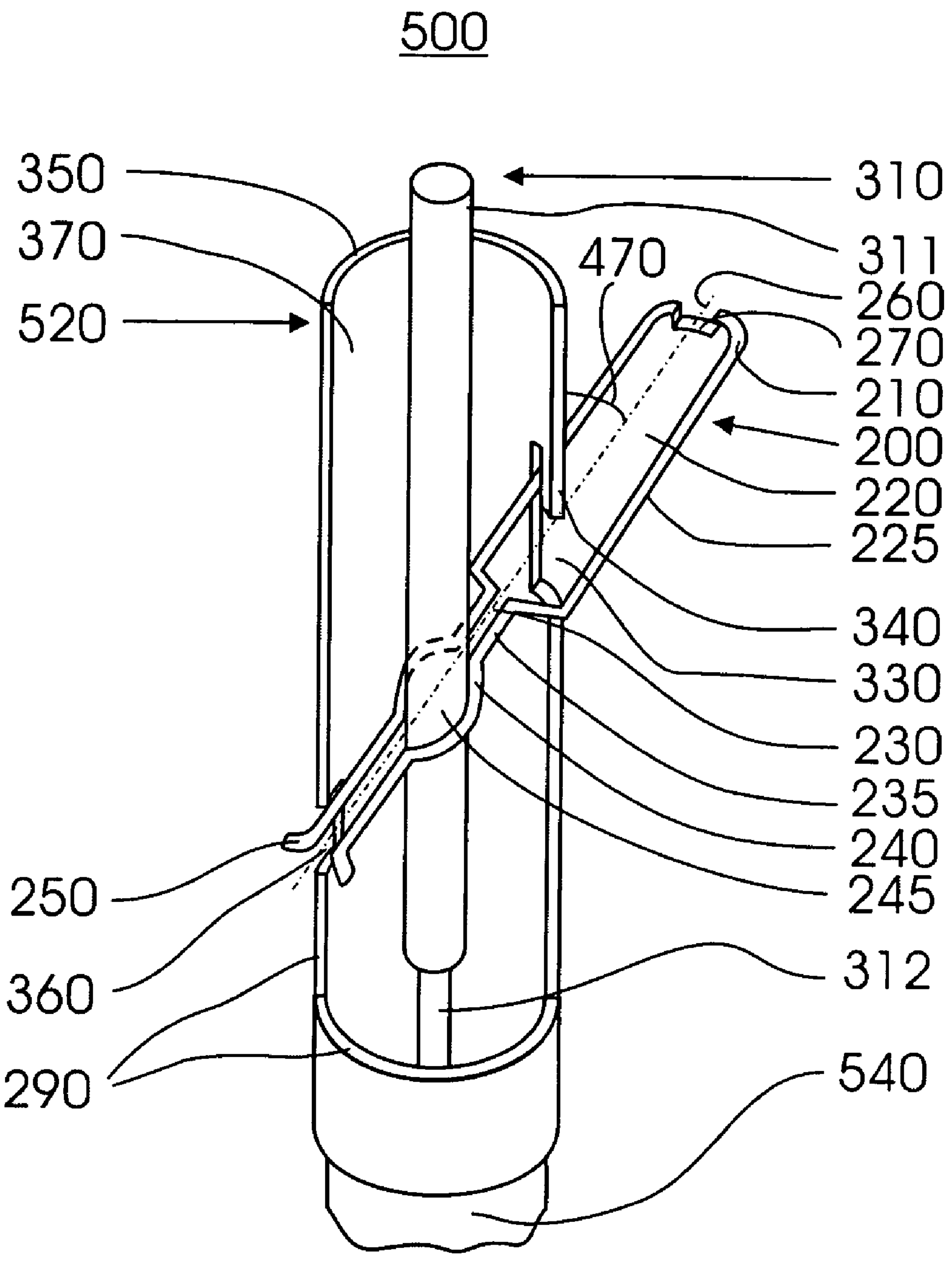

FIG. 4 (includes FIGS. 4A and 4B) are isometric views of the embodiment in FIG. 1, where FIG. 4A shows the dispensing system before the needle is released and FIG. 4B shows the dispensing system after the needle is released. FIGS. 4A and 4B show a tubular open ended guide tube with its front partially removed to illustrate the acupuncture needle encased inside the guide tube and the clip extending inside the guide tube and projecting from two windows; and FIG. 5 is an isometric view of another embodiment of the invention, which embodiment is referred to herein as a cap-on embodiment. This figure shows a tubular cap joins with a guide tube, with the cap front partially removed to illustrate a needle encased in the joined cap and tube, and a clip projecting from two windows of the cap.

It should be understood that the sizes of the different components in the figures may not be in proportion and are shown for visual clarity and for the purpose of explanation.

DETAILED DESCRIPTION OF PREFERRED EMBODIMENTS

FIG. 1 is an embodiment of an acupuncture needle dispensing system 300 incorporating the invention. It enables a one-hand only operation. While two embodiments of the invention are being described, a slide-through and a cap-on, it is the slide-through embodiment that is being explained first. However the cap-on embodiment to be described later works the same.

In the slide-through arrangement of the FIG. 1 embodiment a single hand is shown holding the guide tube 320 with two fingers, while a third finger, an index finger as shown here, manipulates a generally flexible clip 200 of the invention. As can be seen the acupuncture needle 310 is normally secured or held in a narrow enclosure defined by a pair of members of narrow bend 235 of the clip 200 (see FIGS. 2, 3 and 4). The index finger pushes down on a protuberance 270 on a bridge 210 of the clip 200 to move the needle from this narrow enclosure 230 or 245 to a wide enclosure 220 defined by a pair of members of wide bend 225 and a bridge 210 of the clip. The bridge is connected with the ends of the pair of members of the wide bend. Within the wide enclosure the longitudinal or elongated needle is loose for dispensing or insertion into a human by longitudinally passing through the wide enclosure in the clip.

In other words, the clip 200 can be easily manipulated by the protuberance 270 of the bridge 210 to move up and down, providing the operator with good control of the needle 310. The clip substantially resides inside the guide tube 320, and its top end extends through a window 330 on the tube.

Figure 3:
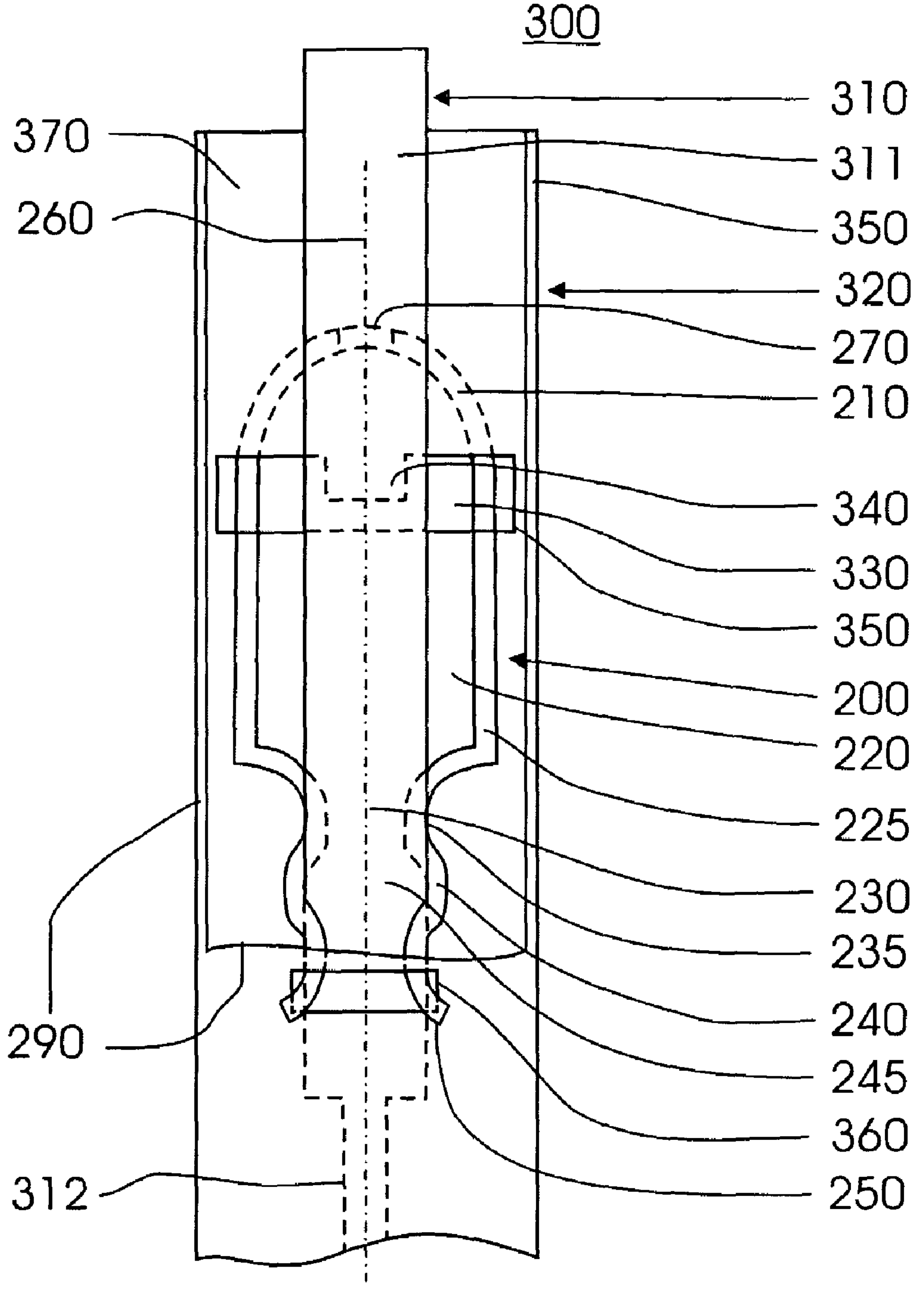
FIG. 3 is a side view of the slide-through embodiment of FIG. 1, showing a tubular guide tube with its front partially removed to illustrate the clip and the acupuncture needle housed in the tube.

The mutual relationships between the guide tube 320, the clip 200 and the needle 310 are further illustrated in the frontal view of FIG. 3 and the isometric views of FIG. 4 (FIGS. 4A and 4B). FIG. 4A shows the needle 310 secured by the narrow enclosure 245 of the clip 200, and FIG. 4B shows the needle loose in the wide enclosure 220 of the clip.

In FIG. 1 the guide tube has been initially placed over an acupoint of a human for the needle to access. Once the needle 310 is free from the clip 200, the index finger of the operator or any other finger or fingers chosen by such operator, can manipulate the needle 310 to more precisely position the sharp tip of the needle through the open end of the guide tube over the skin of a human above an acupoint.

The present system allows the freed longitudinal needle to move freely axially and laterally within the hollow core of tube 320. During the dispensing or insertion of the needle into a human, there is only light contact between the needle and the inner wall of the tube that results in small frictional force. The interaction of the tube and the needle results only in a light frictional force because of the light contact between the tube and the freed longitudinal needle. This small frictional force generally does not interfere with the precise positioning of the sharp tip 313 of the needle 310 on skin 110 above the acupoint.

Generally the efficacy of an acupuncture treatment improves with more precise targeting of an acupuncture needle to an acupoint. The ability of the present system to enable the needle to move freely axially and laterally inside the tube results in the needle being engaged on the skin at a precise position above an acupoint. Further the flexibility of the needle is well utilized in controlling the angle the needle makes with the skin. The operator selects a certain angle to press on the needle handle such that the needle shaft and sharp tip exit from the tube at an optimal angle of skin penetration for a particular acupoint.

Figure 2:
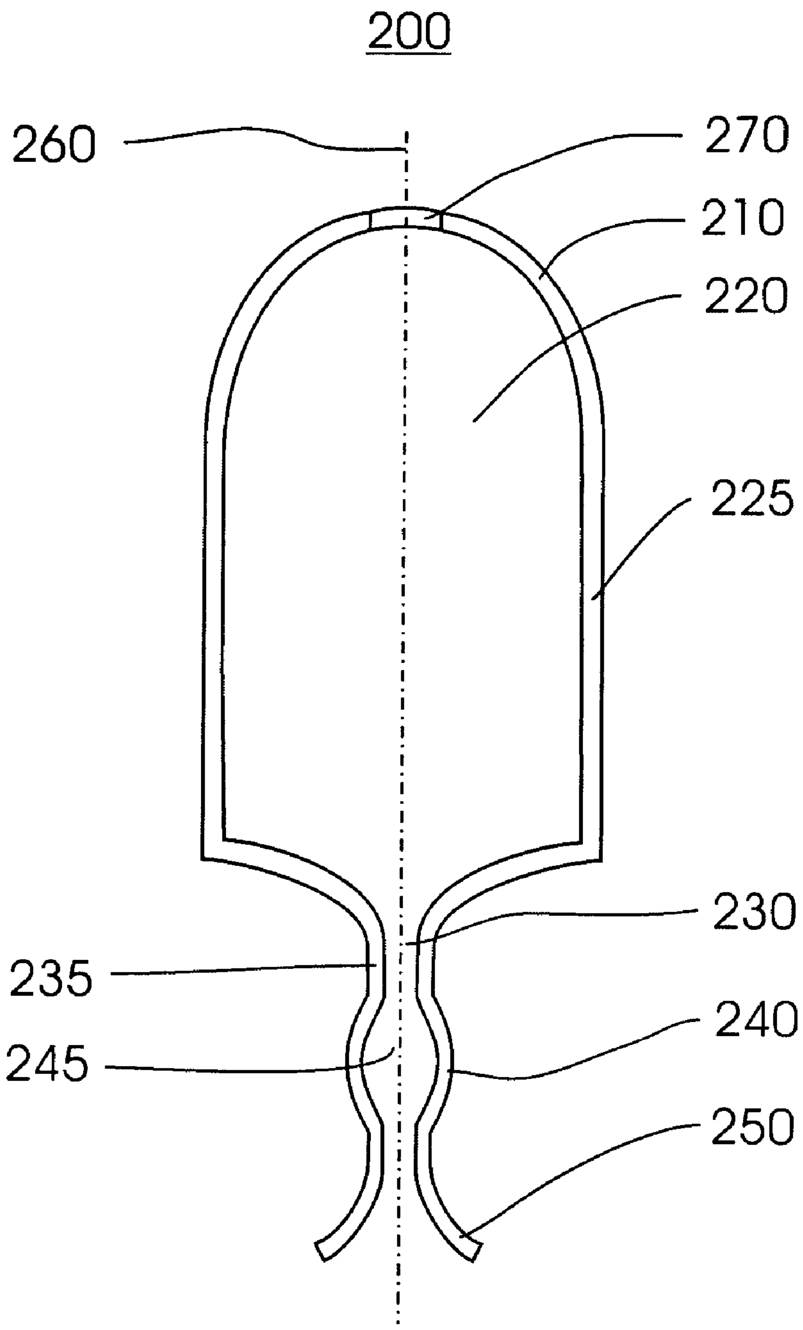
FIG. 2 is a top view of a clip of the embodiment in FIG. 1, emphasizing that the clip has a small bend to secure an acupuncture needle and a wide bend to release the needle.

As best seen in FIG. 2 the narrow bend 235 consists of two substantially symmetrical members 235. These two members are mirror images around a centerline or axis represented at 260. The wide bend 225 consists of two substantially symmetrical members 225 and is also symmetrical around an axis of symmetry 260 of the clip. The clip is most desirably made of a material selected from the group consisting of metal, plastic and a combination of metal and plastic for good flexibility. The clip con be manufactured from software instructions.

FIG. 3 is a side view showing the acupuncture needle 310, clip 200 and the circular guide tube 320 that houses both the needle and clip. In FIG. 3 the front of the guide tube 320 is partially removed as shown by reference numeral 290 for the purpose of illustrating details inside the tube. FIG. 3 further shows the guide tube and the encased needle in the upright and normal position, with the handle 311 of the needle 310 at the top, and therefore above the shaft and tip of the needle.

Although the clip 200 may be of various configurations and materials, it is most simply made from an integral wire. The wire is most desirably made from a material selected from the group consisting of metal, plastic or a combination of metal and plastic for sufficient mechanical strength to retain its shape. This clip is relatively rigid with some flexibility when a force is applied as best seen in FIG. 1. The narrow bend can be equipped with a pair of detents 240 enclosing a space 245 to further define a location to secure the needle. A minimum of one detent on the symmetrical members 235 creates a space 245, but it is preferable to have two detents. While the pair of detents in this embodiment has an arc-shape as illustrated, the pair of detents could define an inverted V-shape enclosing a space or any general shape that provides a recess or enclosure to capture or secure a needle. The enclosed spacings 230 and 245 are sized to be smaller than the diameter of the acupuncture needle in order for the narrow bend to grip firmly on the needle.

As illustrated in FIG. 2 the clip 200 has a wide bend 225 enclosing a space 220 that is sized larger than the diameter of the handle of the needle. The wide bend joins the narrow bend 235 on the distal side. The wide bend has two symmetrical members 225 connected to a bridge 210 on the proximal end of the clip for handling. Alternatively, the bridge could connect the wide bend. The bridge 210 has a selective protuberance 270 that further facilitates handling. It can be seen that with this arrangement, when an acupuncture needle passes through the wide bend it moves freely axially and laterally within the space 220 enclosed by the wide bend 225.

The acupuncture needle 310 has a longitudinal shape and has a handle 311 integral with a shaft 312 as shown in FIG. 4. The shaft terminates with a sharp tip 313 on its distal end. While the specific structure of the needle is not important for this invention, however, the needle included in this embodiment is made of a hard metal such as stainless steel. For different applications, the diameter of the shaft of an acupuncture needle may vary substantially, but generally the diameter is similar to the diameter of a fine sewing needle. As is typical, the handle of the needle on the proximal side for handling has a diameter larger than the diameter of the shaft, which shaft is generally flexible. Upon a light tap on the handle, the sharp tip on the shaft easily penetrates the epidermis of the skin. When a hand continues to push on the needle, the needle continues to penetrate through the epidermis to reach an acupoint below the skin.

The guide tube 320 has a longitudinal body, a hollow core and two open ends. In accordance with conventional practice, the guide tube is typically circular in cross-section and is made from a hard plastic. In keeping with the invention the clip and the guide tube are individually color coded to represent the type of acupuncture needle encased in the tube. Different colors may be used for other types of needles.

The tube 320 has a length that is shorter than the acupuncture needle 310. When the clip 200 holds or secures the needle 310 in the tube, the sharp tip 313 of the needle is positioned inside the tube and the handle 311 extends beyond the tube through an open end. A hand presses upon the handle to insert the needle through the skin of a human for acupuncture treatment. In an upright or normal position of the guide tube encasing the needle, the handle of the longitudinal needle is above the shaft and tip of the needle. In this upright or normal position of the guide tube, the lower window through which the narrow bend of the clip extends is below the higher window through which the bridge of the clip extends.

As illustrated in FIGS. 4A and 4B, the clip 200 has an axis 260 extending in the tube 320 at an oblique angle to the longitudinal axis of the tube so that it projects through an upper window 330 and a lower window 360 in such tube, The lower window 360 has a height to allow the clip to extend outside of the tube. The lower window 360 has a width such that prior to the narrow bend capturing or securing needle 310, the narrow bend which is selectively equipped with one or more curved ends 250 extends easily outside of the lower window. When the narrow bend secures the needle, the width of the lower window is sufficient to allow the narrow bend to extend laterally outside the tube. Most desirably in this extended position, the ends are curved away from one another. While one outwardly curved end 250 widens the narrow bend, it is preferable to have two outwardly curved ends 250 to interact with the lower window or constrain the clip from retracting from the lower window in the guide tube. Also, the width of the lower window 360 is smaller than the width between the two members 225 of the wide bend, constraining the clip 200 from falling out of the lower window and separating from the tube.

The upper window 330 has a height allowing the clip to extend outside of the tube. Such upper window 330 has a width such that the entire clip passes through it. To secure the acupuncture needle in the clip, such needle is inserted into the guide tube from an open end and through the space 220 enclosed by the wide bend of the clip. Then a finger or mechanism pushes or pulls the clip up, preferably by the protuberance 270 on the bridge 210. This action draws the needle against the inner tube wall. The continued pushing or pulling of the clip forces the needle to slide from the wide enclosure or space 220 enclosed by the wide bend 225 into the narrow enclosure or space 230 enclosed by the narrow bend 235. When the narrow bend is equipped with a pair of detents 240 as shown, the needle slides into the enclosure or space 245 enclosed by the detents as the clip is pushed or pulled towards the window 330.

After the narrow bend secures a needle, the bridge 210 and part of the wide bend 225 extend outside the upper window 330. When the guide tube is oriented sideways or upside down, a feature in the tube prevents the clip from sliding out of the tube. This feature is a barrier 340 that is positioned on the upper edge of the upper window 330. When the slide-through embodiment is in a normal and upright position the upper window 330 of the guide tube is above the lower window 360, and the sharp tip of the acupuncture needle points downwards.

In this specific embodiment, the barrier 340 does not extend the full height of the upper window. The barrier has a height sufficient to prevent the clip from sliding out of the tube, yet allows the clip to enter the upper window 330 with a push on the bridge 210. When the barrier has the full height of the upper window, it has a width such that both members of the narrow bend 235 of the clip 200 pass through the two halves of the divided upper window 330 to enter the guide tube by topping on the bridge 210. The full height barrier 340 prevents the narrow bend from retracting from the tube unless a force pulls or pushes it, hence keeping the clip in the tube after dispensing the needle and preventing the creation of unsightly debris or contamination.

Now that the detailed structure has been described, it is useful to review the operation to dispense the needle. An exemplary mode of one hand operation is illustrated. An acupuncture needle is secured by the narrow bond of the clip prior to placing the present system in a package. When an operator removes the present system from its package to start an acupuncture treatment, the operator grips the guide tube with a hand using two fingers. The operator positions the distal open end of the guide tube, vertically or at an angle as required, on a skin area above an acupoint. Then a third finger from the same hand, usually the index finger, presses on the bridge 210 to push the clip down. The clip in turn pushes the needle already secured by the narrow bend against the inner wall of the guide tube 320 and moves the needle from the narrow bend to the wide bend where it is released into the enclosure or space 220.

The handle of the needle is above the shaft and extends beyond the top open end of the tube. The operator freely manipulates the needle 310 by the handle 311 axially and laterally in the space 220 of the wide bend 225 of the clip 200 inside the tube. The operator locates the optimal point on the skin for the needle to penetrate and manipulates the needle to place the sharp tip 313 over the optimal point. A finger from the some hand holding the tube taps on the handle of the needle to engage the sharp tip with the epidermis of the skin.

With the sharp tip engaged on the skin, the operator adjusts an angle for needle penetration by pushing a finger at the handle of the needle with generally axial and lateral forces to create a bend in the flexible needle inside the wide enclosure 220. This bend results in an angle on the shaft at the engagement point on the skin, which angle is also the exit angle of the shaft at the open end of the tube. Next the operator pushes, inserts or dispenses the needle further into the skin so that it is secured in the skin.

Occasionally the needle makes contact with the tube wall, with a light contact resulting in minimal friction that generally allows the operator good control of the needle. The operator removes the guide tube that still houses the clip by sliding the tube over and past the needle. The operator then completes the needle penetration through the skin by pushing the handle of the needle to access the acupoint.

FIG. 4 (includes FIGS. 4A and 4B) are isometric views of the acupuncture needle dispensing system. FIGS. 4A and 4B show a tubular guide tube 320 with its front partially removed as indicated by reference numeral 290 for the purpose of illustrating more clearly the acupuncture needle 310 encased inside the guide tube 320 and the clip 200 extending inside the guide tube and projecting from two windows 330 and 360. FIGS. 4A and 4B illustrate the upper window 330 showing a partial view of the barrier 340 and a part of the window 330 as already shown in FIG. 3. FIGS. 4A and 4B also illustrate a partial view of the lower window 360 as already shown in FIG. 3. Both FIGS. 4A and 4B illustrate the clip extending through two windows in an open ended tubular structure also called the longitudinal guide tube, which guide tube contains an acupuncture needle.

FIG. 4A shows the acupuncture needle 310 encased inside the guide tube and secured by the narrow bend within the enclosure or space 245 shaped by a pair of detents 240 of the clip. FIG. 4B shows after the clip is pushed down into the tube, the acupuncture needle 310 encased inside the guide tube is moved from the enclosure or space 245 shaped by the narrow bend into the enclosure or space 220 shaped by the wide bend.

Since the wide bend is sized to be larger than the handle 311 of the needle, the needle is free to move axially and laterally in the spacing 220 enclosed by the wide bend. The longitudinal axis 260 of the clip makes an oblique angle 470 with the longitudinal axis of the tube. This angle is preferably at 30 degrees. The tube 320 has an outer diameter and wall 350 of a thickness such that the hollow core 370 is sized to allow the needle 310 to move freely axially and laterally.

The curved ends 250 of the clip project beyond the lower window and constrain the clip from retracting out of the tube. While one outwardly curved end 250 constrains the clip at the lower window from retracting out of the tube, it is preferable to have two outwardly curved ends 250.

It is useful to review the slide-through embodiment that is a needle release and dispensing system including an acupuncture needle for eventual dispensing, a means defining guide tube encasing the needle, and a means for securing and releasing the needle for eventual dispensing, whereby one hand can perform the operation. Moreover, the means for securing and releasing the needle for eventual dispensing is manufactured from software instructions, although it is recognized it can be manufactured without software instructions.

FIG. 5 is an isometric view of a cap-on embodiment 500 of the acupuncture needle dispensing system. It shows a tubular open ended cap with its front partially removed as shown by reference numeral 290 for the purpose of illustrating more clearly the acupuncture needle encased inside the joined cap and guide tube and the clip extending inside the cap and projecting from two windows 330 and 360. The cap-on embodiment includes a longitudinal, open ended tubular cap 520 that has an outer diameter, an inner diameter and a wall 350 such that a hollow core 370 cooperates with, joins with or fits over a longitudinal guide tube 540 at their open ends to form a longitudinal tubular structure with a hollow core 370 and open ends.

The cap-on embodiment 500 includes a tubular cap 520 with open ends and a hollow core 370, a tubular guide tube 540 with a hollow core and open ends, an acupuncture needle 310 and a clip 200 for securing and releasing the needle. The cap joins with the guide tube to form a substantially longitudinal tubular structure with open ends. One method of joining is the cap fitting over the guide tube. Another method of joining is fastening the tubular ends of the cap and the guide tube by a fastener such as an adhesive.

The longitudinal or elongated acupuncture needle is encased in the cap that joins with a guide tube that faces the skin of a human, with the shaft and sharp tip of the needle inside the guide tube. The handle of the needle is above the shaft and extends beyond the top open end of the cap. The total length of a cap-on embodiment 500 is similar to the total length of a slide-through embodiment 300 for the same type of acupuncture needle. The total lengths of a slide-through embodiment and a cap-on embodiment may vary for different types of acupuncture needle.

The cap 520 is typically made from metal, plastic, or a combination of metal and plastic. The cap can be manufactured from software instructions. In an example, the tubular shaped cap 520 fits tightly over a guide tube. The cap in FIG. 5 has an upper window 330 that corresponds to the upper window 330 in the slide-through embodiment of FIGS. 3 and 4 and a lower window 360 that corresponds to the lower window 360 in the slide-through embodiment of FIGS. 3 and 4. A clip 200 having a longitudinal axis 260 extends in the cap and projects from the upper window 330 and lower window 360. The longitudinal axis 260 of the clip makes an oblique angle 470 to the longitudinal axis of the cap. This angle is preferably at 30 degrees. In keeping with the invention the clip, the cap and the guide tube are individually color coded to represent the type of acupuncture needle encased in the cap and tube. Different colors may be used for other types of needles.

The cap-on embodiment 500 has the same features and functions to secure and dispense an acupuncture needle with a clip and to retain the clip in the cap after needle dispensing as the slide-through embodiment 300 that has been previously described. FIG. 5 illustrates the clip extending through two windows in an open ended tubular structure also called a cap for the longitudinal guide tube, which cap contains an acupuncture needle.

When the cap is oriented sideways or upside down, a feature in the cap prevents the clip from sliding out of the cap. This feature is a barrier 340 that is positioned on the upper edge of the upper window 330. When the barrier 340 has a partial height of the upper window 330, the barrier 340 has a width that is wider than the width of the narrow bend. The barrier has a height sufficient to prevent the clip from sliding out of the cap, yet allows the clip to enter the upper window 330 with a push on the bridge 210. When the barrier has the full height of the upper window, it has a width such that both members of the narrow bend 235 of the clip 200 pass through the two halves of the divided upper window 330 to enter the cap by tapping on the bridge 210. The full height barrier 340 prevents the narrow bend from retracting from the cap unless a force pulls or pushes it, hence keeping the clip in the cop after dispensing the needle and preventing the creation of unsightly debris or contamination.

When the cap-on embodiment is in a normal and upright position the upper window of the cap is above the lower window, the cap is above the guide tube it joins with, and the sharp tip of the acupuncture needle points downwards.

It is useful to review the cap-on embodiment that is a needle release and dispensing system including an acupuncture needle for eventual dispensing, first means defining a cap and guide tube encasing the needle, and second means for securing and releasing the needle for eventual dispensing, wherein one hand can perform the operation. At least part of the first means defining a cap and guide tube is manufactured from software instructions. In addition, the second means for securing and releasing the needle is also manufactured from software instructions.

It is to be understood that the specific embodiments of the invention that have been described are merely illustrative of certain applications of the principle of the present invention. Numerous modifications may be made to the improved acupuncture needle dispensing system for a needle to be dispensed precisely by a single hand while retaining the clip in the guide tube or cap described herein without departing from the spirit and scope of the present invention.

What is claimed is:

1. A clip in combination with an elongated acupuncture needle encased longitudinally within a guide tube for eventual release, and to facilitate needle insertion, comprising:

a first enclosure sized to secure the acupuncture needle;

a second enclosure wider than the first enclosure, and sized to allow the acupuncture needle to pass longitudinally therethrough; and a bridge that provides for the second enclosure;

wherein:

the first enclosure is shaped by a first bend;

the second enclosure is shaped by a second bend;

the bridge connects with the second bend;

a first window is provided in the guide tube through which the first bend of the clip extends, and the second bend of the clip is wider than the said first window so that the clip remains in the guide tube after the acupuncture needle is released from the clip, such first bend having at least one selective curved end to prevent the clip from pulling inside the tube;

a second window is provided in the guide tube through which the second bend of the clip extends;

the acupuncture needle is secured in the said first bend prior to use;

whereby:

one hand can perform the functions of holding the guide tube, releasing the needle from the clip, and longitudinally launching the acupuncture needle; and a finger can be used to push the clip into the guide tube to move the acupuncture needle from the first bend to the second bend to dispense the acupuncture needle from the guide tube.

2. The clip of claim 1 wherein:

the clip forms an oblique angle relative to the guide tube; and the second window is above the first window when the guide tube is in a normal and upright position.

3. The guide tube of claim 1 wherein the second window of the guide tube has a barrier to prevent separation of the clip from the guide tube.

4. The clip of claim 1 wherein the second bend of the clip is shaped to allow the acupuncture needle to exit the guide tube at an angle.

5. The clip of claim 1 wherein the guide tube is coded with a color to indicate the type of acupuncture needle encased in the tube.

6. A clip for an elongated acupuncture needle encased longitudinally within a cap that joins with a guide tube for eventual release of the needle, comprising:

a first enclosure sized to secure the acupuncture needle;

a second enclosure wider than the first enclosure, and sized to allow the acupuncture needle to pass longitudinally therethrough; and a bridge that provides for the second enclosure;

wherein:

the first enclosure is shaped by a first bend;

the second enclosure is shaped by a second bend;

the bridge connects with the second bend;

a first window is provided in the cap through which the first bend of the clip extends, and the second bend of the clip is wider than the said first window so that the clip remains in the cap after the acupuncture needle is released from the clip, such first bend having at least one selective curved end to prevent the clip from pulling inside the cap;

a second window is provided in the cap through which the second bend of the clip extends;

the acupuncture needle is secured in the said first bend prior to use;

the cap is made from a material selected from the group consisting of metal, plastic and a combination of metal and plastic;

whereby:

one hand can perform the functions of holding the cap that joins with the guide tube, releasing the needle from the clip, and longitudinally launching the acupuncture needle; and a finger can be used to push the clip into the cap to move the acupuncture needle from the first bend to the second bend to dispense the acupuncture needle from the cap that joins with the guide tube.

7. The clip of claim 6 wherein:

the clip forms an oblique angle relative to the cap; and the second window is above the first window when the cap is in a normal and upright position.

8. The guide tube of claim 6 wherein the second window of the cap has a barrier to prevent separation of the clip from the cap.

9. The clip of claim 6 wherein the second enclosure of the clip is shaped to allow the acupuncture needle to exit the guide tube at an angle.

10. The clip of claim 6 wherein the cap is coded with a color to indicate the type of acupuncture needle encased in the cap.

11. The clip of claim 6 wherein the guide tube is coded with a color to indicate the type of acupuncture needle encased in the cap.

12. The clip of claim 1 wherein an acupuncture needle is provided with the clip and the clip extends through two windows in an open ended longitudinal guide tube for said needle, said clip being sized for securing and releasing said acupuncture needle.

13. The clip of claim 6, wherein an acupuncture needle is provided with the clip and the clip extends through two windows in an open ended cap for a longitudinal guide tube for said needle, said clip being sized for securing and releasing said acupuncture needle.

14. An acupuncture needle dispensing system, comprising:

an elongated acupuncture needle for eventual release;

a longitudinal guide tube encasing the acupuncture needle;

a clip for the encased elongated acupuncture needle, comprising:

a first enclosure sized to secure the acupuncture needle;

a second enclosure wider than the first enclosure, and sized to allow the acupuncture needle to pass longitudinally therethrough;

a bridge providing for the second enclosure and having a protuberance to facilitate handling;

wherein:

the needle moves from the first enclosure to the second enclosure for release;

the first enclosure of the clip is shaped by at least one detent defining a position for securing an elongated acupuncture needle; and the clip is made from a material selected from the group consisting of metal, plastic and a combination of metal and plastic wherein: the first enclosure is shaped by a first bend; the second enclosure is shaped by a second bend; and the bridge connects with the second band; and wherein: a first window is provided in the guide tube through which the first bend of the clip extends, and the second bend of the clip is wider than the said first window so that the clip remains n the guide tube after the acupuncture needle is released from the clip, such first bend having at least one selective curved end to prevent the clip from pulling inside the tube; a second window is provided in the guide tube through which the second bend of the clip extends; the acupuncture needle is secured in the said first bend prior to use;

whereby: one hand can perform the functions of holding the guide tube, releasing the needle from the clip, and longitudinally launching the acupuncture needle; and a finger can be used to push the clip into the guide tube to move the acupuncture needle from the first bend to the second bend to dispense the acupuncture needle from the guide tube.

15. The clip of claim 14 wherein:

the clip forms an oblique angle relative to the guide tube; and the second window is above the first window when the guide tube is in a normal and upright position.

16. The clip of claim 14 wherein an integral wire provides for the first and second enclosures.

17. The guide tube of claim 14 wherein the second window of the guide tube has a barrier to prevent separation of the clip from the guide tube.

18. The clip of claim 14 wherein the second enclosure of the clip is shaped to allow the acupuncture needle to exit the guide tube at an angle.

19. The clip of claim 14 wherein the clip and the guide tube are individually coded with a color to indicate the type of acupuncture needle encased in the tube.

20. An acupuncture needle dispensing system, comprising:

an elongated acupuncture needle for eventual release;

a cap that joins with a longitudinal guide tube encasing the acupuncture needle;

a clip for the encased elongated acupuncture needle, comprising:

a first enclosure sized to secure the acupuncture needle;

a second enclosure wider than the first enclosure, and sized to allow the acupuncture needle to pass longitudinally therethrough;

a bridge providing for the second enclosure and having a protuberance to facilitate handling;

wherein:

the needle moves from the first enclosure to the second enclosure for release;

the first enclosure of the clip is shaped by at least one detent defining a position for holding an elongated acupuncture needle;

the clip is made from a material selected from the group consisting of metal, plastic and a combination of metal and plastic; and the cap is made from a material selected from the group consisting of metal, plastic and a combination of metal and plastic wherein: the first enclosure is shaped by a first bend; the second enclosure is shaped by a second bend; and the bridge connects with the second band; and wherein: a first window is provided in the guide tube through which the first bend of the clip extends, and the second bend of the clip is wider than the said first window so that the clip remains n the guide tube after the acupuncture needle is released from the clip, such first bend having at least one selective curved end to prevent the clip from pulling inside the tube; a second window is provided in the guide tube through which the second bend of the clip extends; the acupuncture needle is secured in the said first bend prior to use;

whereby: one hand can perform the functions of holding the guide tube, releasing the needle from the clip, and longitudinally launching the acupuncture needle; and a finger can be used to push the clip into the guide tube to move the acupuncture needle from the first bend to the second bend to dispense the acupuncture needle from the guide tube.

21. The clip of claim 20 wherein:

the clip forms an oblique angle relative to the cap; and the second window is above the first window when the cap is in a normal and upright position.

22. The clip of claim 20 wherein an integral wire provides for the first and second enclosures.

23. The cap of claim 20 wherein the second window of the cap has a barrier to prevent separation of the clip from the cap.

24. The clip of claim 20 wherein the second enclosure of the clip is shaped to allow the acupuncture needle to exit the guide tube at an angle.

25. The clip of claim 20 wherein the cap is coded with a color to indicate the type of acupuncture needle encased in the cap.

26. The clip of claim 20 wherein the guide tube is coded with a color to indicate the type of acupuncture needle encased in the cap.

27. The clip of claim 20 wherein the clip is coded with a color to indicate the type of acupuncture needle encased in the cap.

* * * * *